United States Patent [19]
Jaedicke

[11] 4,268,444
[45] May 19, 1981

[54] PREPARATION OF POLYENE-ALDEHYDES
[75] Inventor: Hagen Jaedicke, Ludwigshafen, Fed. Rep. of Germany
[73] Assignee: BASF Aktiengesellschaft, Ludwigshafen, Fed. Rep. of Germany
[21] Appl. No.: 94,986
[22] Filed: Nov. 16, 1979
[30] Foreign Application Priority Data
Nov. 25, 1978 [DE] Fed. Rep. of Germany ....... 2851051
[51] Int. Cl.³ ..................... C07C 45/45; C07D 319/04
[52] U.S. Cl. .................................. 260/340.7; 568/433; 568/447; 568/446; 568/459; 568/460
[58] Field of Search ................ 260/598, 601 R, 340.7; 568/433, 447, 446, 459, 460

[56] References Cited
U.S. PATENT DOCUMENTS

| | | | |
|---|---|---|---|
| 3,673,284 | 6/1972 | Nagata et al. | 260/598 |
| 3,793,375 | 2/1974 | Schwieter et al. | 260/598 |
| 3,906,047 | 9/1975 | Sumatis et al. | 260/598 |
| 3,953,435 | 4/1976 | Hayashi et al. | 260/598 |
| 3,997,529 | 12/1976 | Olson | 260/598 |

OTHER PUBLICATIONS
House, "Modern Synthetic Reactions", pp. 682–709, (1972).

Primary Examiner—Natalie Trousof
Assistant Examiner—James H. Reamer
Attorney, Agent, or Firm—Oblon, Fisher, Spivak, McClelland & Maier

[57] ABSTRACT

A process for the preparation of polyene-aldehydes, derived from 2,6-dimethyl-2,4,6,8-nonatetraen-1-al by substitution in the 9-position, by means of the Wittig ylide synthesis. The process is based on the observation, contrary to all expectation, that on reacting 2,6-dimethyl-octa-2,4,6-triene-1,8-dial with an equimolar amount of an ylide, it is exclusively the 8-al group of the dialdehyde which reacts. This specificity of the reaction is of particular importance for the preparation of the food dye β-apo-8'-carotinal.

5 Claims, No Drawings

PREPARATION OF POLYENE-ALDEHYDES

The present invention relates to a generally applicable, novel process for the preparation of polyenealdehydes of the general formula I

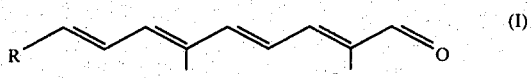

where R is an organic radical.

Specifically, the invention relates to the preparation of the important food dye β-apo-8'-carotinal Ia

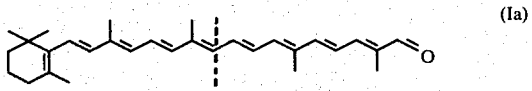

ie. to the preparation of a polyene-aldehyde where R is the $C_{19}$ radical of the left-hand side of the above formula.

Polyene compounds are in general prepared in accordance with the Wittig ylide synthesis by reacting the ylide of a phosphonium salt or of a phosphonate with a carbonyl compound. β-apo-8'-Carotinal has also been synthesized from various structural units (cf. Otto Isler "Carotenoids;" Bäuser Verlag Basel and Stuttgart 1971, pages 445–448). All these syntheses have in common the difficulty that a reaction in which two aldehyde groups are present is involved, namely the aldehyde group which is intended to react with the ylide and the aldehyde group which is intended to remain preserved in the apocarotinal. The latter aldehyde group therefore had to be protected by acetalization, as is known from the example of the following reaction (loc. cit.):

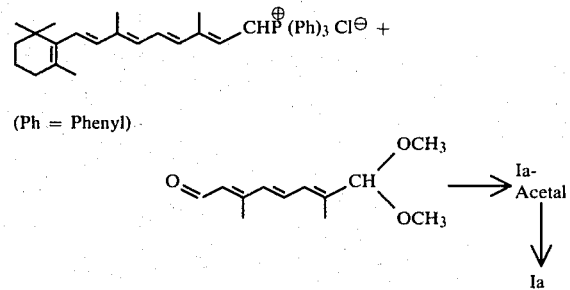

(Ph = Phenyl)

The fact that this procedure is involved does not require elaboration, particularly since the problem of the specific reaction of an aldehyde group is merely shifted, above, the problem of specific acetalization on one side of the molecule only.

It is an object of the present invention to provide a simpler method of preparation then the conventional methods for the polyene-aldehydes I, including in particular β-apo-8'-carotinal Ia.

We have found, surprisingly, that this object is achieved and that a polyene-aldehyde of the general formula I

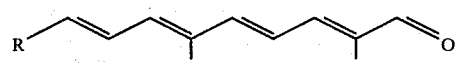

where R is an organic radical is obtained with very high selectivity if 2,6-dimethyl-octa-2,4,6-triene-1,8-dial II

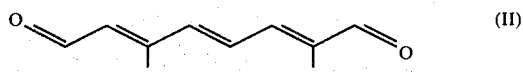

is reacted with an equimolar or about equimolar amount of an ylide of the general formula III

where the radicals R' are identical or different organic radicals, or with a compound of the general formula IV

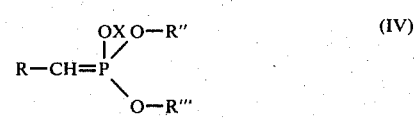

where R" and R'" are identical or different organic radicals and X is a cation.

This process is notable in that it is contrary to all expectation that in this synthesis, under the stated stoichiometric conditions, only the 8-al group of the dialdehyde II reacts. This specificity of the reaction is of outstanding importance, since the reaction of the 1-al group of the dialdehyde II with III or IV would result in an isomer of I, which it would be virtually impossible to separate from the desired product. As far as the preparation of β-apo-8'-carotinal Ia is concerned, the reaction according to the invention would no longer be acceptable if more than about 4% of the 1-al groups would react instead of 8-al groups, since the limit of saleability of the foodstuff grade of the dye β-apo-8'-carotinal corresponds to 96% purity, ie. a 96% content of the natural form. It is obvious that in principle it is of advantage to employ II and III in about equimolar amounts. This is however not absolutely essential since—as already described above—virtually no 1-ylidization occurs, as long as the 8-ylidization is not yet complete. Accordingly, if II is present in excess over III or IV, the latter compounds are exclusively converted to compound I, from which the excess II can as a rule be separated off. A slight excess of the ylide of the phosphonium salt or phosphonate can also be advantageous, for technological reasons, since in that case complete conversion to I first takes place, after which I may react further to give the doubly ylidized dialdehyde II. This secondary product, which in most cases is undesirable, can as a rule be successfully removed from the crystalline mixture if it constitutes only a small proportion.

The process according to the invention is of particular importance in respect of the preparation of Ia. This is not only the case because of the specific one-sided ylide reaction, but also because the ylide IIIa

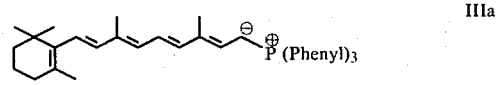

required as the starting compound is available in industrial amounts from the synthesis of vitamin A (axerophtol), by utilizing the vitamin A final liquors. For this purpose, it is merely necessary to convert these liquors, which contain either vitamin A or its acetate, in the conventional manner to the phosphonium salt by means of an acid HX and a tertiary phosphine PR$_3'$, which phosphonium salt can then be converted to the ylide IIIa by reaction with a proton acceptor. The production of axerophthyl phosphonates or their ylides from the vitamin A final liquors for the purpose of preparing β-apo-8'-carotinal is less advantageous.

It is true that the dialdehyde II required as the starting compound is mentioned on page 410 in the monograph on "Carotenoids" referred to above, but to the best of our knowledge it has not previously been characterized in more detail. It may be obtained by conventional methods. For example, it is obtained by a Wittig reaction of a 3-methyl-fumarodialdehyde-1-monoacetal with a 4,4-dimethoxy-3'-methyl-but-2-en-1yl-triphenylphosphonium salt, followed by hydrolysis.

The phosphorylides of the general formula III can be prepared in the conventional manner, for example by treating the phosphonium salts, from which they are derived, with a strong base. Further details of this reaction may be found, inter alia, in the summarizing publication by Tripett (Quart. Reviews, 17 (1963), 406 et seq.).

For the reaction according to the invention, it is advantageous to prepare the phosphorylide directly from the corresponding phosphonium salt in the solvent envisaged for the Wittig synthesis and, where appropriate, even in the presence of the dialdehyde II. The phosphonium salts required can be prepared in a conventional and simple manner by reacting the corresponding organic halides with the phosphines PR$_3'$, or by reacting the corresponding organic hydroxy compounds and an acid HX with the phosphines PR$_3'$. The tertiary phosphines PR$_3'$ can in principle—as is generally known from the comprehensive investigations of the ylide synthesis—be selected according to choice, because the nature of the reaction is determined by the different reactivities of the two aldehyde groups in compound II and not, or only to a lesser extent, by the reactivity of the phosphonium salts. Since, however, triphenylphosphine is hitherto the cheapest and also does not occasion any particular problems in respect of working up and of environmental pollution, this particular phosphine, which is available in industrial amounts, is preferred.

Preferred acids HX are strong acids, for example hydrogen chloride, hydrogen bromide or sulfuric acid, since, as is also generally known, the phosphonium salts with these anions are more stable to auto-decomposition than are the phosphonium salts with anions of weak acids.

Preferred ylides of the general formula III are those where the R' groups are identical or different aryl radicals or are cyclohexyl.

The bases conventionally used for Wittig syntheses may be employed as strong bases for the preparation of the phosphorylides. If the phosphorylides are prepared directly in the reaction medium required for the Wittig reaction, recommended bases are the alkali metal and alkaline earth metal hydroxides, alkali metal hydrides, alkali metal amides and alkali metal and alkaline earth metal alcoholates.

If, however, the phosphorylides are isolated before the actual reaction, not only the bases mentioned but also such compounds as phenyl-lithium or butyllithium may be used.

Ethylene oxide (cf. Angew. Chem. 80 (1968), 535 et seq.) and excess phosphorylide can also, under certain conditions, serve as the strong base.

Suitable solvents for the preparation of the phosphorylides and for carrying out the Wittig reaction are the solvents conventionally used for Wittig snytheses, for example aliphatic or aromatic hydrocarbons, eg. hexane, octane, cyclohexane, benzene, toluene and xylene and their halogenation products, alcohols, eg. methanol, ethanol, isopropanol, butanols, hexanols, cyclohexanol and cyclooctanol, glycols, ethers, eg. diisopropyl ether, ethylene glycol dimethyl ether, tetrahydrofuran, dimethyltetrahydrofuran and dioxane, and mixtures of the above. Polar organic solvents, eg. methanol, ethanol, formamide, dimethylformamide, N-methylpyrrolidone, hexamethylphosphorotriamide, acetonitrile and dimethylsulfoxide, and mixtures of these solvents, are particularly suitable. The process according to the invention can also be carried out in water or in aqueous mixtures.

Instead of the ylides of the general formula III it is also possible—as is generally known for Wittig reactions—to employ compounds of the formula IV

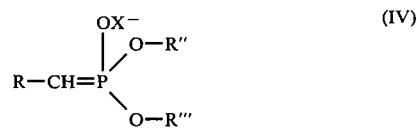

where R" and R'" are alkyl, cycloalkyl, aralkyl or aryl. These compounds are obtaind in the conventional manner, for example by reacting the corresponding halide or tosylate with a triester of phosphorous acid and then reacting the resulting phosphonic acid ester of the formula

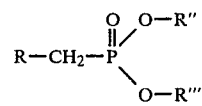

with a strong base as a proton acceptor. The strong bases and solvents which can be used are the same as those which have been described for the preparation of the ylide.

To carry out the reaction, according to the invention, of 2,6-dimethyl-octa-2,4,6-triene-1,8-dial II with an ylide III or a compound IV, it is advantageous to introduce the dial II into a solvent, add an about stoichiometric amount of a strong base, slowly introduce the solution of an ylide or of a compound IV into the resulting suspension at the reaction temperature, and allow the mixture to continue to react for about 1-2 hours. It is however also possible to take a solution of the dial II and of the ylide and to add the strong base in portions thereto, or first to prepare III or IV from the phosphonium salts or phosphonic acid esters with strong bases and to add the dial II slowly to the resulting solution. The reaction temperature can be from about −70° to 100° C., preferably from 0° to +70° C.

Since the Wittig reaction is known per se, it does not require further comment here.

In principle, the radicals R in III or IV can be any organic radicals, so that the process according to the invention presents a novel and advantageous method of obtaining, in principle, all aldehydes of the formula I. For the preparation of carotinoids, carotinoidlike compounds and their precursors and intermediates, compounds I of particular interest are those where R is a saturated or unsaturated $C_1$—$C_{40}$-hydrocarbon radical. In particular, radicals having the carbon skeleton of vitamin A or of fragments thereof are suitable, and in these the carbon chain and the terminal 6-membered ring may carry methyl or ethyl groups as substituents, and the radicals may be conjugated throughout, unsaturated or partially or completely saturated. Radicals of this type with 1 or 2 ethylenically unsaturated bonds or with one or more ether groups, above all in the 6-membered ring, are also of interest for further syntheses.

Finally, the diversity of possible preparations which may be carried out is further increased by the fact that the aldehydes I can, for their part, undergo ylide reactions with phosphonium salts or phosphonates. All these syntheses, by means of which the structural element

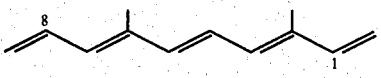

is to be introduced into carotinoids, are substantially simplified by the process according to the invention, in that first an 8-linkage and, if desired, thereafter a 1-linkage is formed, without auxiliary operations.

EXAMPLE 1

Preparation of β-apo-8'-carotinal (Ia)

A suspension of 2.6 g (15.83 millimoles) of 2,6-dimethyl-2,4,6-octatriene-1,8-dial, 1.85 g of magnesium hydroxide powder and 50 ml of toluene was boiled and a solution of 10.0 g (15.90 millimoles) of axerophthyltriphenylphosphonium bisulfate (IIIa) in 30 ml of methanol was added in the course of 60 minutes. The mixture was heated for a further 30 minutes and, after cooling, was acidified with dilute acetic acid. 20 ml of water were then added to the reaction mixture and the aqueous phase was separated off. The toluene solution was washed with twice 50 ml of 60% strength aqueous dimethylformamide and with 30 ml of water at 60° C. The toluene was then distilled off under reduced pressure until the residual volume was 12 ml, after which 54 ml of methanol and 3.2 ml of 30% strength by volume aqueous sulfuric acid were added. After stirring for 24 hours at room temperature, 4.55 g of pure β-apo-8'-carotinal were separated off.

EXAMPLE 2

Preparation of 2,6,11-trimethyl-11-(4,4-dimethyl-2,6-dioxan-1-yl)-dodecapenta-2,4,6,8,10-en-1-al A solution of 2.9 g (6.21 millimoles) of 3-(4,4-dimethyl-2,6-dioxan-1-yl)-but-2-en-1-yl-triphenylphosphonium chloride

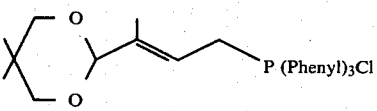

in 8 ml of methanol was added, in the course of 30 minutes, to a boiling suspension of 1 g (6.09 millimoles) of II, 15 ml of toluene and 0.93 g of calcium hydroxide powder, and the batch was then refluxed for a further 2 hours. After it had cooled, the mixture was acidified with aqueous acetic acid, and the organic phase was then worked up by a method similar to that of Example 1. On concentrating the toluene solution, the above aldehyde, having the structure

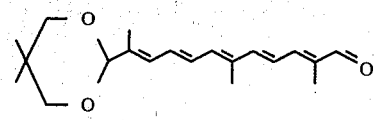

was obtained as a crystalline residue, in 95% yield. This is a novel compound.

$^1$H-NMR (CDCl$_3$ as solvent; TMS as internal standard; δ in ppm): 9.46 (s, 1H); 6.2–7.2 (m, 7H); 4.81 (s, 1H); 3.6 (4H); 1.9–2.1 (9H); 1.25 (s, 3H) and 0.78 (s, 3H).

I claim:

1. A process for the preparation of a polyene-aldehyde of the formula I:

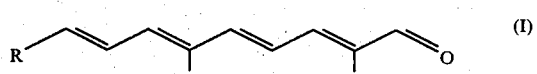

where R is selected from the group consisting of a saturated or unsaturated $C_1C_{40}$ hydrocarbon,, and a radical having the carbon skeleton of vitamin A or fragments thereof, which radical may or may not be substituted by methyl, ethyl and ether groups, may or may not be conjugated throughout, and may be unsaturated or partially or completely saturated; which comprises:

reacting 2,6-dimethyl-octa-2,4,6-triene-1,8-dial of the formula

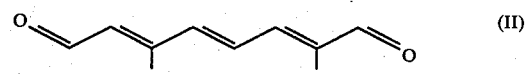

with an equimolar or about equimolar amount of a compound selected from the group consisting of an ylide of the formula III:

and a compound of the formula IV:

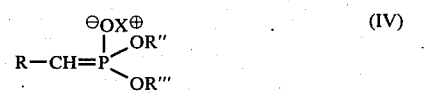

wherein

R', R" and R''' are the same or different alkyl, cycloalkyl, aralkyl or aryl radicals;

and X$^+$ is the cationic component of a strong base.

2. A process as claimd in claim 1, wherein the ylide of an axerophthyl-phosphonium salt is reacted with compound II to give β-apo-8'-carotinal of the formula:

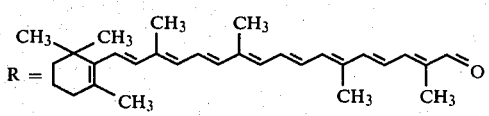

3. The process of claim 1, wherein R'=R"=R'''=phenyl.

4. The process of claim 1, wherein X is selected from the group consisting of alkali metals and alkali earth metals.
5. The process of claim 1, wherein R has the formula:
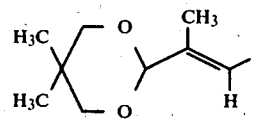
* * * * *